(12) United States Patent
Long et al.

(10) Patent No.: US 11,578,286 B2
(45) Date of Patent: *Feb. 14, 2023

(54) UV CURE BASECOATINGS FOR MEDICAL DEVICES

(71) Applicant: Biocoat, Incorporated, Horsham, PA (US)

(72) Inventors: Tyler Richard Long, Royersford, PA (US); Casmir S Ilenda, Southampton, PA (US)

(73) Assignee: Biocoat, Incorporated, Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/663,942

(22) Filed: May 18, 2022

(65) Prior Publication Data

US 2022/0275300 A1 Sep. 1, 2022

Related U.S. Application Data

(63) Continuation of application No. 17/075,931, filed on Oct. 21, 2020, now Pat. No. 11,359,156.

(60) Provisional application No. 62/923,712, filed on Oct. 21, 2019.

(51) Int. Cl.

| | | |
|---|---|---|
| *C10M 107/28* | (2006.01) |
| *C08F 220/18* | (2006.01) |
| *C08F 220/14* | (2006.01) |
| *C10M 107/42* | (2006.01) |
| *C10M 107/36* | (2006.01) |
| *A61L 29/14* | (2006.01) |
| *C10N 40/00* | (2006.01) |
| *C10N 50/00* | (2006.01) |
| *A61L 29/08* | (2006.01) |
| *A61L 31/10* | (2006.01) |

(52) U.S. Cl.
CPC .......... *C10M 107/28* (2013.01); *A61L 29/14* (2013.01); *C08F 220/14* (2013.01); *C08F 220/1804* (2020.02); *C08F 220/1808* (2020.02); *C08F 220/1811* (2020.02); *C08F 220/1812* (2020.02); *C10M 107/36* (2013.01); *C10M 107/42* (2013.01); *A61L 29/085* (2013.01); *A61L 31/10* (2013.01); *A61L 2400/10* (2013.01); *A61L 2420/08* (2013.01); *C10M 2209/0845* (2013.01); *C10M 2209/123* (2013.01); *C10M 2217/0245* (2013.01); *C10M 2217/0285* (2013.01); *C10N 2040/50* (2020.05); *C10N 2050/023* (2020.05)

(58) Field of Classification Search
CPC ...... A61L 29/14; A61L 31/10; A61L 2400/10; A61L 2420/08; C08F 220/14; C08F 220/1804; C08F 220/1808; C08F 220/1811; C08F 220/1812; C10M 107/28; C10M 107/36; C10M 107/42; C10M 2209/0845; C10M 2209/123; C10M 2217/0245; C10M 2217/0285; C10N 2040/50; C10N 2050/023

See application file for complete search history.

(56) References Cited

U.S. PATENT DOCUMENTS 11,359,156 B2 * 6/2022 Long ................ C08F 220/1812
2018/0244927 A1 * 8/2018 McCoy .................. A61L 31/10

FOREIGN PATENT DOCUMENTS

WO WO-2018237224 A1 * 12/2018 ............. B32B 27/12

* cited by examiner

*Primary Examiner* — James C Goloboy
(74) *Attorney, Agent, or Firm* — BakerHostetler

(57) ABSTRACT

The invention concerns coating composition comprising hydrophobic polymer for use as a photoreactive basecoat for a medical device or implant comprising a polymer made from monomers comprising: (a) 1 to 12 mol % of at least one photoactive monomer that is a hydrogen atom abstracter and (b) 99 to 88 mol % of one or more of acrylamides, methacrylamides, acrylates, methacrylates, and N-vinylpyrrolidone; wherein the polymer has a glass transition temperature (Tg) of less than 40° C.

21 Claims, No Drawings

UV CURE BASECOATINGS FOR MEDICAL DEVICES

CROSS-REFERENCE

This application is a continuation of U.S. patent application Ser. No. 17/075,931, filed Oct. 21, 2020, which is a non-provisional application of and claims priority to and the benefit of U.S. Provisional Application No. 62/923,712, filed Oct. 21, 2019, which are incorporated herein by reference in their entirety.

TECHNICAL FIELD

The invention concerns ultraviolet light curable basecoating for medical devices and implants.

BACKGROUND

The present invention relates to the field of non-thrombogenic and lubricious coatings that are applied to medical devices, especially devices intended to be implanted, temporarily or permanently, in the body and in blood-contact applications.

Among the many advances in medical practice in recent years is the development of medical devices that supplement the surgeon's skills. Examples of these are a variety of vascular catheters and guide wires that can be used to treat remote areas of the circulatory system otherwise available only by major surgery. Another is the stent, a device that reinforces arterial walls and prevents occlusion after angioplasty. Another is the intra-ocular lens that restores youthful eyesight to the elderly afflicted with cataracts. Heart valves, artificial pacemakers, and orthopedic implants are among a lengthening list of other such devices.

Nearly all of the above-described devices are constructed of plastics and metals that were never intended to invade and sometimes reside for prolonged periods in the human body. They present surfaces that bear little or no resemblance to those of human organs, which are generally hydrophilic, slippery and biocompatible.

Equally important for devices that must be inserted and moved through body tissues is their lubricity. Most metals and plastics have poor lubricity against body tissues, which results in mechanical abrasion and discomfort when the device is passed over the tissue.

The surfaces of devices designed and manufactured from such materials can be made biocompatible, as well as hydrophilic and slippery, by properly designed coatings. Thus, the way has been opened to construct medical devices from conventional plastics and metals having the particular physical properties required, and then to apply suitable coatings to impart the desired properties to their surfaces.

It has been shown that polymers that have low coefficients of friction when wet are water soluble polymers that are cross-linked or otherwise immobilized and swell, but do not dissolve, upon exposure to water. Polysaccharides have been shown to be useful in making hydrophilic, lubricious coatings on substrates. Such coatings are described in U.S. Pat. Nos. 4,801,475, 5,023,114, 5,037,677, and 6,673,453, the disclosures of which are hereby incorporated by reference. Lubricious coatings based upon polysaccharides exhibit exceptional biocompatibility and lubricity, but relatively poor resistance to ionizing radiation.

It is desirable for some applications to have a lubricious coating made of a synthetic polymer for the benefits of a longer shelf-life and stability to radiation-sterilization processes. Hydrophilic synthetic polymers, such as poly(acrylic acid) and its copolymers have often been proposed to make lubricious, hydrophilic coating because of their ability to generate a hydrated layer on the surface.

Contacting blood with a foreign object having a plastic or metal surface induces a complex set of clot-forming reactions that occur at the blood surface interface. Thromboembolism is a major complication associated with the clinical use of artificial devices, such as catheters, guidewires, mechanical heart valves, ventricular assist devices, implantable artificial hearts, vascular grafts, etc. In particular, thromboembolism is an important complication of angiographic procedures, particularly with catheter and guidewire manipulations proximal to the brachiocephalic vessels.

Surface modification is commonly used to make the materials more blood-compatible, while minimizing any loss of mechanical properties. Two approaches to modification have been commonly used. Suppression of nonspecific protein adsorption using coatings of polyethylene oxide (PEO) (a neutral, hydrophilic, and highly flexible polymer) or other hydrophilic polymers has been investigated for surface passivation. Uncontrolled, nonspecific protein adsorption, which usually occurs within seconds following the exposure of a foreign surface to blood, can initiate blood coagulation and the complement pathways.

A second approach has been to use coatings that actively assist the anticoagulant activity of surfaces. Certain plasma proteins (such as antithrombin (AT) which can inhibit thrombin and factor Xa (FXa)) or heparin (a glycosaminoglycan which catalyzes the reactions of plasma AT) have been used for this purpose. Frech et al., in "A Simple Noninvasive Technique to Test Nonthrombogenic Surfaces," The American Journal of Roentgenology, vol. 113 (1971), p. 765-768, discloses coating of a guidewire with a benzalkonium-heparin complex. Ovitt et al., in "Guidewire Thrombogenicity and Its Reduction", Radiology, vol. 111 (1974), p. 43-46, reports Teflon coated guidewires treated with benzalkoniumheparin. U.S. Pat. No. 4,349,467 (William) shows the application of heparin to solid polymeric resin substrates by steeping the substrate in a solution of ammonium salt and contacting the substrate with a heparin salt solution.

There have also been many attempts to invent hydrophilic polymers with applications ranging from electrophoresis, hair treatment and paper treatment. As revealed by Albarghouthi et al, in "Poly-N-hydroxyethylacrylamide(polyDuramide): A novel, hydrophilic, self-coating polymer matrix for DNA sequencing by capillary electrophoresis", Electrophoresis, vol. 23 (2002), p. 1429-1440, non-ionic monomers, such as N-hydroxyethyl acrylamide, have great hydrophilicity.

The following references, namely WO10041527A, WO10041530A, WO11125713A, JP2011046619A, JP2011046652A, JP2010126482A, and JP2010090049A, teach copolymers comprised of a 5-30 mol % of a carboxylic acid monomer and 70-95 mol % of an alcohol containing acrylic monomer for use in hair treatment formulations. These patent applications do not disclose the utility of the copolymers as lubricious, biocompatible coatings nor do they disclose their resistance to ionizing radiation. JP2006176934A teaches copolymers from methacrylamide, hydroxyethyl acrylamide, and an ionic vinyl monomer for use as an additive to increase the strength of the paper. The latter reference does not disclose the utility of the copolymers as lubricious, biocompatible coatings nor does it disclose their resistance to ionizing radiation.

Typically, a basecoat resides between the substrate and the lubricious coating in a medical device or implant. The basecoat can improve stability of the lubricious coating. There is a need in the art for improved basecoats, such as ones that provide a more rapid binding of the lubricious topcoat. A basecoat that binds to the hydrophilic topcoat through ultraviolet (UV) cure would meet this need.

SUMMARY

In some embodiments, the invention concerns coating compositions comprising hydrophobic polymers for use as a photoreactive basecoat for a medical device or implant comprising a polymer made from monomers comprising:

(a) 1 to 12 mol % of at least one photoactive monomer that is a hydrogen atom abstracter and (b) 99 to 88 mol % of one or more of acrylamides, methacrylamides, acrylates, methacrylates, and N-vinylpyrrolidone; wherein the polymer has a glass transition temperature (Tg) of less than 40° C.

In certain embodiments, the basecoats additionally comprise a multifunctional aziridine. (a) 95-99.8 wt % of the hydrophobic polymer described herein; and (b) 0.2-5 wt % multifunctional aziridine.

The invention also concerns medical devices or implants comprising a photoreactive basecoat comprising a coating composition described herein. In preferred composition, the basecoat is hydrophobic. In some embodiments, the device or implant contains a hydrophilic topcoat where the basecoat resides on a substrate and the topcoat resides on the basecoat.

In other embodiments, the invention concerns coating solutions comprising a coating composition described herein and a solvent.

In yet another embodiment, the invention concerns method of coating substrates. In some embodiments, both a basecoat and a topcoat are applied to a substrate. When both the basecoat and the topcoat are cured by UV light, either (a) the basecoat is applied and cured before the topcoat is added or (b) the basecoat is applied and dried, the topcoat is added and, then, both the basecoat and topcoat are cured by UV light.

DETAILED DESCRIPTION OF ILLUSTRATIVE EMBODIMENTS

The requirements for any coating intended for use on medical devices will be set forth and explained first. The specification will then show how the present invention fulfills these requirements.

The coatings of the instant invention are suitable for use in medical devices. The coating of the present invention has the following properties:

(1) the coating must be able, on drying, to form a continuous, adherent film of good integrity on the surface of the material to be coated. This means that the minimum film-forming temperature of the coating solution must be lower than the expected drying temperature to be used during device fabrication;

(2) the formed polymer film must be flexible and adherent enough to conform without rupture to the bending and twisting of the coated device under the expected conditions of use;

(3) when the coated device is immersed for long periods in aqueous media such as human blood, the film must not weaken or lose its integrity;

(4) the coating must present a non-cytotoxic and blood compatible surface. When contacted with human blood the coating must not initiate blood coagulation and the complement pathways;

(5) the coating must be firmly and securely bound to the substrate so that no particles or fragments or leachable components can contaminate an aqueous medium such as human blood; and (6) the coating must withstand some acceptable form of sterilization without loss of integrity, durability, or biocompatibility.

A coating which satisfies the above requirements is made as described below.

The present disclosure may be understood more readily by reference to the following description taken in connection with the accompanying Figures and Examples, all of which form a part of this disclosure. It is to be understood that this disclosure is not limited to the specific products, methods, conditions or parameters described and/or shown herein, and that the terminology used herein is for the purpose of describing particular embodiments by way of example only and is not intended to be limiting of any claimed disclosure. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to methods of operating a device and systems and to the devices and systems providing said methods. That is, where the disclosure describes and/or claims a coating composition, medical device, coating solution or method, it is appreciated that these descriptions and/or claims also describe and/or claim the devices, equipment, or systems for accomplishing these methods.

In some embodiments, the invention concerns coating compositions comprising hydrophobic polymer for use as a photoreactive basecoat for a medical device or implant comprising a polymer made from monomers comprising:

(a) 1 to 12 mol % of at least one photoactive monomer that is a hydrogen atom abstracter, and (b) 99 to 88 mol % of one or more of acrylamides, methacrylamides, acrylates, methacrylates, and N-vinylpyrrolidone; wherein the hydrophobic polymer has a glass transition temperature (Tg) of less than 40° C.

In some embodiments, the invention concerns coating compositions comprising hydrophobic polymer for use as a photoreactive basecoat for a medical device or implant comprising a polymer made from monomers comprising:

(a) 1 to 5 mol % of at least one photoactive monomer that is a hydrogen atom abstracter, and (b) 99 to 95 mol % of one or more of acrylamides, methacrylamides, acrylates, methacrylates, and N-vinylpyrrolidone; wherein the hydrophobic polymer has a glass transition temperature (Tg) of less than 40° C.

Preferred polymers have a glass transition temperature of less than 40° C., 20° C., 15° C. or 10° C.

In preferred embodiments, the photoactive monomer that is a hydrogen atom abstracter is a benzophenone compound. In certain embodiments, the photoactive monomer that is a hydrogen atom abstracter comprises one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, and 2-hydroxy-4-methacryloxyethoxybenzophenone.

The monomers copolymerized with the photoactive monomer may be one or more acrylate, methacrylate, or other monomers known to copolymerize well with them. In certain embodiments, the polymer comprises methacrylate of the structure

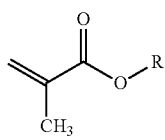

where R is an optionally substituted $C_1$-$C_{20}$ alkyl. In some embodiments, R may be methyl, ethyl, or butyl. Preferably the copolymer will contain monomers such as ethylhexyl, isodecyl, dodecyl or others that contribute to a low glass temperature copolymer. The copolymer also contains monomers with some hydrophilic character to provide good interaction with the topcoat solution and polymer. Examples include hydroxyethyl methacrylate and N-vinylpyrrolidone monomers.

In certain embodiments, the monomer contributing low glass temperature to the hydrophobic polymer is an acrylate having a $C_4$-$C_{20}$ alkyl group, such as butyl acrylate.

In certain embodiments, the basecoat additionally comprises a multifunctional aziridine. In some embodiments, the coating composition comprises (a) 95-99.8 wt % of the hydrophobic polymer; and (b) 0.2-5 wt % multifunctional aziridine. In other embodiments, the coating composition comprises (a) 98-99.5 wt % of the hydrophobic polymer; and (b) 0.5-2 wt % multifunctional aziridine.

The invention also concerns medical devices or implants comprising a photoreactive basecoat comprising a coating composition described herein. In some embodiments, the basecoat resides between a substrate and a hydrophilic topcoat. Some preferred topcoats comprise one or more of polyacrylate, polyvinylpyrrolidones, hyaluronic acid and polyacrylamide. In other embodiments, the topcoat comprises a N-(2-hydroxyethyl)acrylamide and acrylic acid copolymer. Some embodiments comprise a plurality of covalent cross-links between said basecoat and said hydrophilic topcoat.

4-Methacryloxy-2-hydroxy benzophenone (MHB) can be copolymerized with (meth)acrylate monomers to produce a hydrophobic, photoactive polymer. Upon UV cure this polymer functions as a tie layer to bind the substrate to a hydrophilic topcoat layer. Topcoats cured in the presence of this photoactive basecoat bind well even if the topcoat contains no photoactive component.

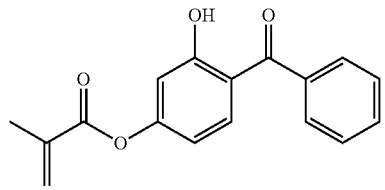

4-methacryloxy-2-hydroxy benzophenone (MHB)

Preferred medical devices include catheters or guide wires.

In yet other aspects, the invention concerns coating solutions comprising 2 to 15 wt % of a coating composition described herein. In other embodiments, the solution comprises 3 to 13 wt % or 4 to 12 wt % or 5 to 10 wt % of a coating composition described herein. In preferred embodiments, the solution comprises an organic solvent. Preferred solvents include one or more of toluene, ethanol, acetone, isopropanol, ethyl acetate, dimethylformamide, tetrahydrofuran, butanol, N-methyl-2-pyrrolidone, n-butyl acetate, 1,2-propanediol monomethyl ether acetate, isobutyl acetate, isopropyl acetate, methyl acetate, 3-methyl-1-butanol, methylethyl ketone, 2-methyl-1-propanol, 1-pentanol, 2-propanol, propyl acetate, dichloromethane, dimethyl sulfoxide, methylbutyl ketone and xylene.

In some aspects, the invention concerns methods of coating articles. Some methods comprise coating a substrate with a basecoat comprising a coating composition described herein. The basecoat may be cured by exposure of the basecoat to UV light. In some embodiments, the basecoat may be coated with a hydrophilic topcoat.

In yet other embodiments, the coating methods include coating a substrate with a basecoat comprising a coating composition described herein, coating the basecoat with a hydrophilic topcoat and curing the basecoat and topcoat UV light. The hydrophilic topcoat can be photoactive (i.e. contain groups that absorb UV radiation and react when exposed to UV radiation), but the presence of photoactive groups in the topcoat is not necessary.

The invention relates to at least the following aspects.

Aspect 1A. A coating composition comprising hydrophobic polymer for use as a photoreactive basecoat for a medical device or implant comprising a polymer made from monomers comprising: (a) 1 to 12 mol % of at least one photoactive monomer that is a hydrogen atom abstracter, and (b) 99 to 88 mol % of one or more of acrylamides, methacrylamides, acrylates, methacrylates, and N-vinylpyrrolidone; wherein the polymer has a glass transition temperature (Tg) of less than 40° C.

The invention relates to at least the following aspects.

Aspect 1B. A coating composition comprising hydrophobic polymer for use as a photoreactive basecoat for a medical device or implant comprising a polymer made from monomers comprising: (a) 1 to 5 mol % of at least one photoactive monomer that is a hydrogen atom abstracter, and (b) 99 to 88 mol % of one or more of acrylamides, methacrylamides, acrylates, methacrylates, and N-vinylpyrrolidone; wherein the polymer has a glass transition temperature (Tg) of less than 40° C.

Aspect 2. The coating composition of aspect 1, additionally comprising a multifunctional aziridine.

Aspect 3. The coating composition of aspect 2, comprising (a) 95-99.8 wt % of the hydrophobic polymer; and (b) 0.2-5 wt % multifunctional aziridine.

Aspect 4. The coating composition of anyone of aspects 1-3, comprising methacrylate of the structure

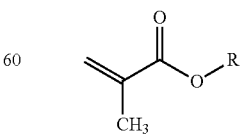

where R is an optionally substituted $C_1$-$C_{20}$ alkyl.

Aspect 5. The coating composition of aspect 4, wherein R is one or more of methyl, ethylhexyl, isodecyl, or dodecyl.

Aspect 6. The coating composition of aspect 4, wherein the hydrophobic polymer comprises hydroxyethyl methacrylate and N-vinylpyrrolidone.

Aspect 7. The coating composition of anyone of aspects 1-6, wherein the hydrophobic polymer comprises acrylate having a $C_4$-$C_{20}$ alkyl group.

Aspect 8. The coating composition of anyone of aspects 1-7, wherein the photoactive monomer that is a hydrogen atom abstracter comprises a benzophenone moiety.

Aspect 9. The coating composition of aspect 8, wherein the photoactive monomer that is a hydrogen atom abstracter comprises one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, and 2-hydroxy-4-methacryloxyethoxybenzophenone.

Aspect 10. The coating composition of anyone of aspects 1-9 having a Tg of less than 20° C.

Aspect 11. A medical device or implant comprising a photoreactive basecoat comprising a coating composition of any one of aspects 1-10.

Aspect 12. The medical device of aspect 11, wherein basecoat resides between a substrate and a hydrophilic topcoat.

Aspect 13. The medical device of aspect 12, wherein the topcoat comprises one or more of polyacrylate, polyvinylpyrrolidones, hyaluronic acid and polyacrylamide.

Aspect 14. The medical device of aspect 12, wherein the topcoat comprises a N-(2-hydroxyethyl)acrylamide and acrylic acid copolymer.

Aspect 15. The medical device of aspect 11, wherein the medical device is a catheter or guide wire.

Aspect 16. The medical device of aspect 12, comprising a plurality of covalent cross-links between said basecoat and said hydrophilic topcoat.

Aspect 17. A coating solution comprising 2 to 15 wt % of a coating composition of any one of aspects 1-10 in a solvent.

Aspect 18. The coating solution of aspect17, wherein the solvent is an organic solvent.

Aspect 19. The coating solution of aspect 18, wherein the solvent comprises one or more of toluene, ethanol, acetone, isopropanol, ethyl acetate, dimethylformamide, tetrahydrofuran, butanol, N-methyl-2-pyrrolidon, n-butyl acetate, 1,2-propanediol monomethyl ether acetate, isobutyl acetate, isopropyl acetate, methyl acetate, 3-methyl-1-butanol, methylethyl ketone, 2-methyl-1-propanol, 1-pentanol, 2-propanol, propyl acetate, dichloromethane, dimethyl sulfoxide, methylbutyl ketone and xylene.

Aspect 20. A method of forming a coated article comprising coating a substrate with a basecoat comprising a coating composition of any one of aspects 1-10.

Aspect 21. The method of aspect 20, additionally comprising curing the basecoat by exposure of the basecoat to UV light.

Aspect 22. The method of aspect 21, additionally comprising coating said basecoat with a hydrophilic topcoat.

Aspect 23. The method of aspect 20, additionally comprising (a) coating said basecoat with a hydrophilic topcoat and (b) curing the basecoat and topcoat with UV light.

EXAMPLES

The invention is illustrated by the following non-limiting examples.

The following abbreviations are used herein:
MHB -4-methacryloxy-2-hydroxybenzophenone was the monomer that provided
photoactivity to the copolymer
BA—butyl acrylate
MMA—methyl methacrylate
HEMA—hydroxyethyl methacrylate
NVP—N-vinyl pyrrolidone
EHMA—ethylhexyl methacrylate
iDMA—isodecyl methacrylate
DDMA—dodecyl methacrylate The coating was applied to a variety of substrates in the form of rods or tubing. The rods were stainless steel or PMMA with a diameter of 0.125 inches. Pebax® 35D and 55D plastic tubing had an outer diameter of 0.079 inches and a wall thickness of 0.005 inches. The tubing was placed over stainless steel rod for stability before coating. The coating process consisted of wiping the rod with isopropyl alcohol, dip coating in basecoat solution at 0.2 in/sec, drying at 60° C. for 10 minutes, dip coating in topcoat solution at 0.2 in/sec, and drying at 60° C. for 10 minutes. Only after all coatings had been applied was the rod subjected to UV radiation.

UV cure was performed in an Uvitron IntelliRay model UV0832 UV Cure unit equipped with a UVA 600 Watt metal halide lamp. Irradiance was measured with an EIT Uvicure Plus II radiometer purchased from INPRO Technologies. This one channel UVA radiometer measures the radiation between 320 and 390 nm.

Two different methods were used to provide uniform radiation around the rods. In the first method hexagonal couplers were attached to the rod to provide a fixed geometry for turning the coated rod as it was being cured. The sample could then be passed through 6 rotations to expose all sides. The rotation pattern was 0°, 120°, 240°, 60°, 180°, and 300°. In the second method a motor provided uniform radiation by continuous rotation at 20 rpm.

Typical radiation times in the examples are 2-30 minutes and typical irradiance is 100-200 milliwatts per square centimeter (mW/cm$^2$) (at 320-390 nm from a UVA metal halide lamp). It is noted that all of the 320-390 nm radiation is not useful in the photo-crosslinking, only the wavelengths that are actually absorbed by the photoactive group can lead to reaction. It is also understood that lower irradiance than that used in these examples can be accommodated by an increase in radiation time.

The friction of the coating was tested on a Chatillon CS225 Force Measurement Machine. It was equipped with a heated water bath and pinch pads that pressed together at a constant force. The water bath is filled PBS solution and heated to 37° C. The pinch pads are submerged in the water and pressed together with 470 g of force. The friction is measured as the grams of force required to push and pull the sample through the pads. The lubricity and durability are determined by averaging the grams of force when the samples are pulled through the pads. Lubricity is the average from cycle 1-3 and durability is the force during cycle 30.

Photoactive topcoats were made by copolymerizing 4-methacryloxy-2-hydroxybenzophenone and low glass temperature (meth) acrylate monomers. Photoactive basecoat polymers synthesized are summarized in table 1.

TABLE 1

Photoactive Basecoat Polymers

| Basecoat Polymer | % MHB | Comonomer | Glass Temperature (degrees C., calculated) |
|---|---|---|---|
| BP-1 | 2 | EHMA | 25 |
| BP-2 | 5 | EHMA | 29 |
| BP-3 | 8 | EHMA | 33 |
| BP-4 | 10 | EHMA | 33 |
| BP-5 | 8 | iDMA | 17 |
| BP-6 | 5 | DDMA/MMA | 6 |
| BP-7 | 8 | DDMA/MMA | 7 |
| BP-8 | 8 | DDMA/BMA | 10 |
| BP-9 | 2 | BA/MMA | 7 |
| BP-10 | 5 | BA/MMA | 8 |
| BP-11 | 8 | BA/MMA | 9 |
| BP-12 | 5 | BA | −8 |
| BP-13 | 0 | BA/MMA | 12 |

Basecoat Polymers also contain 12.7% HEMA and 21.7% NVP

Poly(methyl methacrylate) (PMMA) rods were coated with Basecoat Polymer BP-5 and polyvinylpyrrolidone (PVP) topcoat (Aldrich 1,300,000 molecular weight by light scattering). The coated rods were cured at an irradiance of 186 mW/cm$^2$ through each of six rotations. After pinch testing, the rods were rinsed for 10 seconds under running cold tap water, immersed in 0.5% Congo Red aqueous solution, and then rinsed again for 10 seconds. The presence of bound PVP indicated by the intense red color demonstrated that grafting had occurred between the photoactive basecoat and the PVP topcoat.

PVP topcoat with four different UV cure basecoat polymers were tested over PMMA substrate rods. UV cure was done at an irradiance of 166 mW/cm$^2$ over 20 minutes at each of the six rotations. Although the samples exhibited fair lubricity, they only lasted 10-20 cycles. The results are summarized in table 2.

TABLE 2

UV Cure with PVP Topcoat and Different Basecoat Polymers

| Basecoat Polymer | Basecoat Monomer | First cycle friction | Last cycle friction |
|---|---|---|---|
| BP-3 | EHMA | 53 | 66 |
| BP-5 | iDMA | 38 | 62 |
| BP-7 | DDMA/MMA | 77 | 94 |
| BP-11 | BA/MMA | 72 | 95 |

A Hydrophilic Acrylic Polymer and blends of this Hydrophilic Acrylic Polymer with PVP were evaluated as topcoats (with added surfactant). The Hydrophilic Acrylic Polymer (HAP) was a copolymer of acrylic acid and 2-hydroxyethylacrylamide. The UV cure was six rotations at an irradiance of 180 mW/cm$^2$. The results are in table 3. All three rods of each sample exhibited good lubricity and durability through 30 cycles.

TABLE 3

Effect of Cure Time on Coating Performance of HAP/PVP Topcoat Blends

| Topcoat | Cure time, minutes | Initial Friction | 30th Cycle Friction | Bound Topcoat, micrograms/cm$^2$ |
|---|---|---|---|---|
| HAP + PVP | 6 × 30 | 17.3 | 16.5 | 44 |
| HAP | 6 × 30 | 21.3 | 11.6 | 71 |
| HAP + PVP | 6 × 15 | 6.32 | 4.8 | 38 |
| HAP | 6 × 15 | 6.17 | 4.8 | 63 |
| HAP + PVP | 6 × 5 | 9.02 | 4.8 | 7.8 |
| HAP | 6 × 5 | 9.876 | 19.9 | 11.8 |

Basecoat Polymer for all samples was BP-3 (EHMA) coated at 8% Solids.

Bound topcoat measures HAP portion of the bound topcoat

The results summarized in the above examples do indicate that good lubricity and durability can be obtained from a photoactive basecoat without any photoactivity in the topcoat. A disadvantage of the UV cure process used in these examples is that it requires stopping the UV cure and manually rotating the samples five times during the cure. To overcome this a motor was set up to continuously rotate the samples at 20 rpm during the cure. This is expected to provide even more uniform UV cure around the circumference of the rod or tubing. This method was not only more convenient, but as shown below provided even better lubricity and durability at even shorter cure times.

Table 4 shows a comparison of several compositions using different monomer compositions and different amounts of the photoactive monomer. Results indicate that a variety of low glass temperature monomers can be used to provide a lubricious, durable coating. These examples have no photoactive component in the topcoat.

TABLE 4

Effect of Amount of Photoactive Monomer and of Comonomer Composition

| Basecoat Polymer | Basecoat Solids | Cure Time, minutes | Dynamic Friction, g, Cycles 1-3 | Dynamic Friction, g, 30$^{th}$ Cycle | Bound Topcoat, micrograms/cm$^2$ |
|---|---|---|---|---|---|
| BP-3 | 8% | 2 | 24 | >340 | 0.8 |
| BP-3 | 8% | 6 | 18 | 270 | 1.3 |
| BP-3 | 8% | 20 | 12 | 59 | 9.6 |
| BP-3 | 10% | 20 | 14 | 17 | 39 |
| BP-4 | 8% | 20 | 10 | 15 | 39 |
| BP-11 | 8% | 20 | 12 | 17 | 36 |
| BP-5 | 8% | 20 | 9 | 17 | 36 |
| BP-7 | 8% | 20 | 10 | 17 | 36 |
| BP-8 | 8% | 20 | 12 | 15 | 37 |
| BP-3 | 8% | 20 | 22 | 22 | 19 |
| BP-3 | 8% | 6 | 21 | 24 | 12 |
| BP-4 | 8% | 6 | 16 | 40 | 11 |
| BP-11 | 8% | 6 | 16 | 17 | 10 |
| BP-11 | 8% | 2 | 18 | 260 | 4.5 |
| BP-3 | 8% | 2 | 16 | 320 | 3.3 |
| BP-7 | 8% | 2 | 15 | 260 | 2.8 |
| BP-7 | 8% | 6 | 12 | 240 | 5.2 |
| BP-8 | 8% | 2 | 16 | 290 | 1.7 |
| BP-8 | 8% | 6 | 16 | 290 | 2.1 |
| BP-1 | 10% | 20 | 14 | 46 | 29 |
| BP-1 | 10% | 6 | 18 | 180 | 25 |
| BP-2 | 10% | 20 | 15 | 20 | 26 |
| BP-2 | 10% | 6 | 13 | 55 | 12 |
| BP-10 | 10% | 20 | 14 | 18 | 24 |
| BP-10 | 10% | 6 | 14 | 34 | 8 |
| BP-9 | 10% | 20 | 14 | 38 | 19 |
| BP-9 | 10% | 6 | 16 | 67 | 4.3 |
| BP-6 | 10% | 20 | 18 | 29 | 8.2 |

TABLE 4-continued

Effect of Amount of Photoactive Monomer
and of Comonomer Composition

| Basecoat Polymer | Basecoat Solids | Cure Time, minutes | Dynamic Friction, g, Cycles 1-3 | Dynamic Friction, g, 30$^{th}$ Cycle | Bound Topcoat, micrograms/cm$^2$ |
|---|---|---|---|---|---|
| BP-6 | 10% | 6 | 17 | 43 | 1.4 |
| BP-12 | 10% | 6 | 17 | 18 | 5.7 |

Footnotes for Table 4:
Basecoat is coated over Pebax ® 55D tubing.
After drying basecoat, Poly(HEAA-co-AA) topcoat containg surfactant was added and dried before UV cure.

Footnotes for Table 4:

Basecoat is coated over Pebax® 55D tubing.

After drying basecoat, Poly(HEAA-co-AA) topcoat containing surfactant was added and dried before UV cure.

Coated rods with even better durability can be obtained by including some trifunctional aziridine such as trimethylolpropane tris(2-methyl-1-aziridine propionate) (Crosslinker CX-100) in the basecoat. Polyfunctional aziridines are known crosslinkers in thermal cure processes. The results in table 5 demonstrate the increase in durability.

TABLE 5

Effect of Trifunctional Aziridine

| Polymer | Basecoat Solids | Trifunctional aziridine | Cure Time, minutes | Dynamic Friction, g, Cycles 1-3 | Dynamic Friction, g, 30$^{th}$ Cycle | Bound Topcoat, micrograms/cm$^2$ |
|---|---|---|---|---|---|---|
| BP-2 | 10% | 0 | 20 | 17 | 28 | 3.5 |
| BP-2 | 10% | 0 | 6 | 18 | 64 | 2.0 |
| BP-2 | 10% | 0.087% | 20 | 17 | 16 | 39 |
| BP-2 | 10% | 0.087% | 6 | 23 | 30 | 52 |
| BP-10 | 10% | 0.0425% | 6 | 22 | 29 | 69 |
| BP-10 | 10% | 0.0425% | 6 (+ heat) | 20 | 21 | 67 |
| BP-10 | 10% | 0.0843% | 6 | 26 | 26 | 66 |
| BP-10 | 10% | 0.0843% | 6 (+ heat) | 26 | 24 | 66 |
| BP-2 | 10% | 0.0845% | 6 | 17 | 124 | 58 |
| BP-2 | 10% | 0.0845% | 6* | 11 | 180 | 40 |
| BP-10 | 10% | 0.0845% | 6 | 16 | 15 | 59 |
| BP-10 | 10% | 0.0845% | 6* | 14 | 23 | 59 |
| BP-6 | 10% | 0.0845% | 6 | 12 | 370 | 56 |
| BP-6 | 10% | 0.0845% | 6* | 15 | 280 | 28 |
| BP-12 | 10% | 0.0845% | 6 | 19 | 16 | 68 |
| BP-12 | 10% | 0.0845% | 6* | 19 | 19 | 63 |
| BP-13 | 10% | 0.082% | 6 | 25 | 240 | 69 |
| 50% BP-13/50% BP-4 | 10% | 0.082% | 6 | 23 | 27 | 58 |
| BP-4 | 10% | 0.082% | 6 | 15 | 14 | 49 |

Footnotes for Table 5:
Basecoat is coated over Pebax ® 55D tubing.
After drying basecoat, a poly(HEAA-co-AA) topcoat was added and dried.
6(+ heat) indicates that the samples were heated at 60° C. for 30 minutes after UV cure.
6* indicates that the sample were soaked in aqueous PBS solution for 18 hours at 50° before pinch testing.

Footnotes for Table 5:

Basecoat is coated over Pebax® 55D tubing.

After drying basecoat, a poly(HEAA-co-AA) topcoat was added and dried.

6 (+heat) indicates that the samples were heated at 60° C. for 30 minutes after UV cure.

6* indicates that the samples were soaked in aqueous PBS solution for 18 hours at 50° C. before pinch testing.

Throughout this specification, words are to be afforded their normal meaning, as would be understood by those skilled in the relevant art, unless otherwise indicated. However, so as to avoid misunderstanding, the meanings of certain terms will be specifically defined or clarified.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value.

Where present, all ranges are inclusive and combinable. That is, references to values stated in ranges include every value within that range including the endpoint values.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A and B," "A and C," "B and C," or "A, B, and C."

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other possible embodiment(s) and such a combination is considered to be another embodiment. Conversely, various features of the invention that are, for brevity, described in the context of a single embodiment, may also be provided separately or in any sub-combination. Further, while an embodiment may be described as part of a series of steps or part of a more general structure, each said step or part may also be considered an independent embodiment in itself As used herein, the terms "article" and "substrate" are not limited to any shape or size, as it may be a layer of material, multiple layers or a block having at least one surface of which is modified by a coating composition described herein.

Glass transition temperature (Tg) is determined using the Fox equation and literature values of the homopolymers. The Fox equation is as follows:

$$1/T_{g,mix} \approx \Sigma_i \omega_i / T_{g,i}$$

where $T_{g,mix}$ and $T_{g,i}$ are the glass transition temperatures in degrees Kelvin of the mixture/copolymer and of the components, respectively, and $\omega$, is the mass fraction of component i. Monomers that produce low $T_g$ homopolymers are required to produce copolymers with low $T_g$'s. Examples include butyl acrylate (Tg=−54 degrees C.), 2-ethylhexyl methacrylate (−10), isodecyl methacrylate (−30), and dodecyl methacrylate (−65). The homopolymer Tg's of some of the other monomers used are 100° C. for MMA, 20° C. for BMA, 120° C. for NVP, 105° C. for HEMA, 143° C. for MHB and 105° C. for acrylic acid.

For two components A and B, the Fox equation reduces to $$1/T_{g,mix} \approx \omega_A/T_{g,A} + \omega_B/T_{g,B}$$

As used herein the term "hydrophobic" refers to a polymer that is not soluble in aqueous solutions. A crosslinked hydrophobic polymer does not swell significantly in water (<50%).

The term "hydrophilic" refers to a polymer that is soluble in water or water-alcohol solutions. A crosslinked hydrophilic polymer swells significantly in aqueous solutions (>100%).

The invention claimed is:

1. A coating composition for use as a photoreactive basecoat for a medical device or implant, the coating composition comprising a photoreactive hydrophobic polymer made from monomers comprising:
   (a) 1 to 6 mol % of a photoactive monomer comprising a benzophenone moiety, and
   (b) 99 to 94 mol % of one or more of N-vinyl-pyrrolidone, and acrylates and methacrylates of the structure

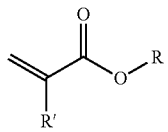

where R is an optionally substituted $C_1$-$C_{20}$ alkyl,
R' is either $CH_3$ or H;
wherein the polymer has a glass transition temperature (Tg) of less than 40° C.

2. The coating composition of claim 1, additionally comprising a multifunctional aziridine.

3. The coating composition of claim 2, comprising
   (a) 95-99.8 wt % of the hydrophobic polymer; and
   (b) 0.2-5 wt % multifunctional aziridine.

4. The coating composition of claim 1, wherein R is one or more of methyl, ethylhexyl, isodecyl, or dodecyl.

5. The coating composition of claim 1, wherein the hydrophobic polymer comprises hydroxyethyl methacrylate and N-vinylpyrrolidone.

6. The coating composition of claim 1, wherein the hydrophobic polymer comprises acrylate having a $C_4$-$C_{20}$ alkyl group.

7. The coating composition of claim 1, wherein the photoactive monomer comprising a benzophenone moiety is selected from 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, 2-hydroxy-4-methacryloxyethoxybenzophenone, and combinations thereof.

8. The coating composition of claim 1 having a Tg of less than 20° C.

9. A medical device or implant comprising a photoreactive basecoat comprising a coating composition of claim 1.

10. The medical device of claim 9, wherein the basecoat resides between a substrate and a hydrophilic topcoat.

11. The medical device of claim 10, wherein the topcoat comprises one or more of polyacrylate, polyvinylpyrrolidones, hyaluronic acid and polyacrylamide.

12. The medical device of claim 10, wherein the topcoat comprises a N-(2-hydroxyethyl)acrylamide and acrylic acid copolymer.

13. The medical device of claim 9, wherein the medical device is a catheter or guide wire.

14. The medical device of claim 10, comprising a plurality of covalent cross-links between said basecoat and said hydrophilic topcoat.

15. A coating solution comprising 2 to 15 wt % of a coating composition of claim 1 in a solvent.

16. The coating solution of claim 15, wherein the solvent is an organic solvent.

17. The coating solution of claim 16, wherein the solvent comprises one or more of toluene, ethanol, acetone, isopropanol, ethyl acetate, dimethylformamide, tetrahydrofuran, butanol, N-methyl-2-pyrrolidon, n-butyl acetate, 1,2-propanediol monomethyl ether acetate, isobutyl acetate, isopropyl acetate, methyl acetate, 3-methyl-1-butanol, methylethyl ketone, 2-methyl-1-propanol, 1-pentanol, 2-propanol, propyl acetate, dichloromethane, dimethyl sulfoxide, methyl-butyl ketone and xylene.

18. A method of forming a coated article comprising coating a substrate with a basecoat comprising a coating composition of claim 1.

19. The method of claim 18, additionally comprising curing the basecoat by exposure of the basecoat to UV light.

20. The method of claim 19, additionally comprising coating said basecoat with a hydrophilic topcoat.

21. The method of claim 18, additionally comprising (a) coating said basecoat with a hydrophilic topcoat and (b) curing the basecoat and topcoat with UV light.

* * * * *